(12) United States Patent
Naidu et al.

(10) Patent No.: US 8,411,814 B2
(45) Date of Patent: Apr. 2, 2013

(54) METHOD OF AND APPARATUS FOR MEASURING CENTER DETECTOR INDEX ON CT SCANNER WITH LIMITED FIELD OF VIEW ACCESS

(75) Inventors: Ram C. Naidu, Newton, MA (US); Sergey B. Simanovsky, Brookline, MA (US); David Schafer, Rowley, MA (US)

(73) Assignee: Analogic Corporation, Peabody, MA (US)

( * ) Notice: Subject to any disclaimer, the term of this patent is extended or adjusted under 35 U.S.C. 154(b) by 157 days.

(21) Appl. No.: 13/126,608

(22) PCT Filed: Oct. 31, 2008

(86) PCT No.: PCT/US2008/082006
§ 371 (c)(1),
(2), (4) Date: Apr. 28, 2011

(87) PCT Pub. No.: WO2010/050970
PCT Pub. Date: May 6, 2010

(65) Prior Publication Data
US 2011/0206180 A1    Aug. 25, 2011

(51) Int. Cl.
*A61B 6/00* (2006.01)
*G06K 9/00* (2006.01)

(52) U.S. Cl. ............. 378/19; 378/20; 378/207; 382/131

(58) Field of Classification Search ............... 378/19, 378/20, 207; 382/131
See application file for complete search history.

(56) References Cited

U.S. PATENT DOCUMENTS

| | | | | |
|---|---|---|---|---|
| 4,812,983 A * | 3/1989 | Gullberg et al. | ................ | 378/14 |
| 4,852,132 A * | 7/1989 | Namikawa | ..................... | 378/19 |
| 5,214,578 A * | 5/1993 | Cornuejols et al. | ........... | 378/207 |
| 5,331,553 A * | 7/1994 | Muehllehner et al. | ... | 250/363.02 |
| 5,450,461 A * | 9/1995 | Hsieh | .............................. | 378/19 |
| 5,717,732 A * | 2/1998 | Tam | ................................... | 378/4 |
| 5,828,718 A * | 10/1998 | Ruth et al. | ...................... | 378/19 |
| 6,422,749 B1 * | 7/2002 | Polkus et al. | ................. | 378/205 |
| 6,813,374 B1 | 11/2004 | Karimi et al. | | |
| 6,850,587 B1 | 2/2005 | Karimi et al. | | |
| 7,062,009 B2 * | 6/2006 | Karimi et al. | .................... | 378/19 |
| 7,187,750 B1 * | 3/2007 | Hsieh et al. | ..................... | 378/19 |

(Continued)

FOREIGN PATENT DOCUMENTS

WO    0236012 A1    5/2002

OTHER PUBLICATIONS

International Search Report cited in related application No. PCT/US2008/082006 dated Jun. 16, 2009.

(Continued)

*Primary Examiner* — Alexander H Taningco
(74) *Attorney, Agent, or Firm* — Cooper Legal Group LLC (57) ABSTRACT

A position of a center detector of a radiation scanner can be determined without shutting down the scanner and/or manually positioning a phantom in the scanning field of the scanner. A phantom, comprising a target, is scanned to create an axial image of the phantom. The target is masked in the axial image, producing a masked axial image of the phantom. The masked axial image is reprojected in projection space, and the axial reprojection is compared to an axial projection or a rebinned axial projection of the phantom that was used to create the axial image. A target axial projection of data related to the masked target, created from the comparison of the axial projection or the rebinned axial projection and the axial reprojection, is used to determine the position of the center detector.

20 Claims, 5 Drawing Sheets

U.S. PATENT DOCUMENTS 7,583,778 B2 * 9/2009 Mori .................................. 378/4

OTHER PUBLICATIONS

Gullberg; et al., "Estimation of geometrical parameters for fan beam tomography", Phys. Med. Biol., 1987, vol. 32, No. 12, 1581-1594, http://csuptwo.com/Journals/Estimation_of_Geometrical_Parameters_for_Fan_Beam_Tomography.pdf.

Sun Y et al: "A calibration method for misaligned scanner geometry in cone-beam computed tomography", NDT & E International, Butterworth-Heinemann, Oxford, GB, vol. 39, No. 6, pp. 499-513, XP025109683 ISSN: 0963-8695 [retrieved on Sep. 1, 2006] p. 503-p. 510.

Noo; et al., "Analytic method based on identification of ellipse parameters for scanner calibration in cone-beam tomography" Physics in Medicine and Biology, vol. 45, 2000, pp. 3489-3508.

* cited by examiner

METHOD OF AND APPARATUS FOR MEASURING CENTER DETECTOR INDEX ON CT SCANNER WITH LIMITED FIELD OF VIEW ACCESS

BACKGROUND

The present application applies to the measurement of the center detector in Computed Tomography (CT) equipment. While it applies to a variety of computed tomography equipment, it finds particular application to security examination equipment, such as baggage systems commonly found in airports.

Computed Tomography, in general, generates a three-dimensional image of an object from a series of two-dimensional measurements taken about a single axis of rotation. An object under examination is exposed to radiation, and images are formed based upon the radiation absorbed by the object, or rather an amount of radiation that is able to pass through the object. Highly dense objects absorb more radiation than less dense objects, and thus an object having a high density, such as a metal gun or bone, for example, will be apparent when surrounded by less dense objects, such as clothing or tissue.

In baggage systems, Computed Tomography equipment is used to detect weapons, explosives, and other prohibited items that may be contained in a bag or suitcase being scanned. One type of CT baggage scanner is described in U.S. Pat. No. 6,256,404 (Gordon et al.). In particular, an x-ray tube and a detector array are mounted on diametrically opposing sides of an annular shaped rotating platform, or disk, disposed within a gantry support for rotation about a single axis that is parallel to the direction of travel of the baggage (e.g., along a conveyor system). The x-ray tube emits x-rays, and the x-rays traverse the baggage under examination. X-rays that are not absorbed by the baggage and/or objects therein are detected by a detector. Data from the detector is used by reconstruction algorithms to create an image of the bag and the contents thereof.

The reconstruction algorithms rely on the value of a center detector to perform calculations that convert the data from the detectors into useful images. In order to mitigate artifacts (e.g., streaks at the edges of objects) on the image, the value of the center detector is periodically calibrated. One technique currently used to calibrate the center detector value is known as pin calibration, the details of which are described in G. T. Gullberg, B. M. W. Tsui, C. R. Crawford and E. Edgerton, "Estimation of geometrical parameters for fan beam tomography", *Physics in Medicine and Biology*, 1987, Vol. 32, No. 12, pp. 1581-1592. On security scanners, pin calibration comprises stopping a conveyor belt and placing a cylindrical pin phantom (e.g., a test article of known, physical configuration) into the scanning field of the scanner (e.g., via a user who has to crawl into the scanner). Offset, air, and phantom data are acquired during an axial scan of the phantom. The data is analyzed to determine a center detector value. It will be appreciated that other phantoms, such as those described in U.S. Pat. No. 6,813,374 (Karimi et al.), may also be used for performing calibrations and tests on a scanner.

While current calibration techniques, such as pin calibration, have proven effective in determining the center detector value, there remains room for improvement. For example, the pin calibration technique requires a dedicated pin phantom with custom mounts. Additionally, a service technician has to crawl into the scanning field of the scanner to position the phantom and remove the phantom once the calibration procedure is over. Thus, the procedure is time consuming and cumbersome to execute because the scanner may not be easily accessible when integrated with entrance and exit conveyor tunnels, for example.

SUMMARY

Aspects of the present application address the above matters, and others. According to one aspect of the present application, a scanner comprises a radiation source configured to emit radiation into a scanning field of the scanner, and a detector array is configured to detect radiation emitted into the scanning field that traverse an object situated therein. The scanner also comprises a scanner calibrator configured to determine a center detector of the detector array based upon a comparison of an axial projection of the object to an axial reprojection of a masked axial image of the object.

According to another aspect of the present application, a target detector system is configured to generate a target axial projection from an axial projection representing a target detected in a scanning field by a detector array in a scanner. The target detector system comprises a rebinner configured to rebin the axial projection to generate a rebinned axial projection, and a reconstructor configured to generate an axial image from the rebinned axial projection. The system also comprises a masking component configured to mask the target in the axial image to generate a masked axial image, a reprojector configured to reproject the masked axial image to generate an axial reprojection, and a target axial projection component configured to compare the axial reprojection to the rebinned axial projection to generate the target axial projection.

According to yet another aspect of the present application, a method of detecting a center detector array of a scanner using a target is provided. The method comprises positioning the target in a scanning field of the scanner and emitting rays into the scanning field toward the detector array. The method also comprising detecting the rays with the detector array to acquire an axial projection and rebinning the axial projection to generate a rebinned axial projection. The method further comprises generating an axial image from the rebinned axial projection, masking the target in the axial image to generate a masked axial image, and reprojecting the masked axial image to generate an axial reprojection. The method also comprises comparing the axial reprojection to the rebinned axial projection to generate the target axial projection and identifying the center detector of the detector array according to the target axial projection.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
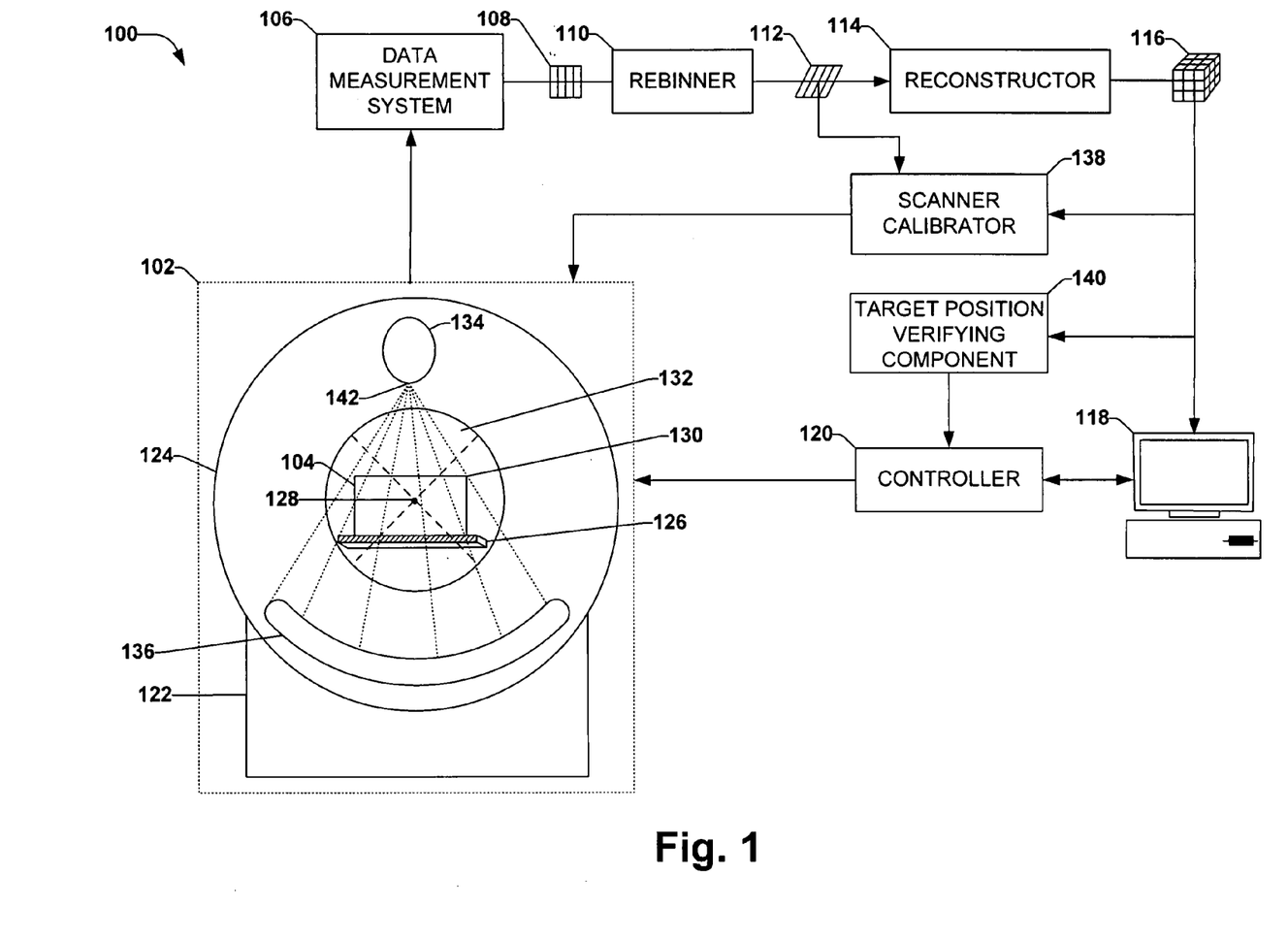
FIG. 1 depicts a scanner wherein the center detector of a detector array may be determined.

FIG. 1 depicts an example scanner 100. The scanner 100 may be used to scan baggage at an airport or government building, for example. As illustrated, the scanner 100 typically comprises a object scanning apparatus 102 configured to scan an object 104 (e.g., a suitcase), a data measurement system 106 configured to generate an axial projection 108 based upon data received from the object scanning apparatus 102, a rebinner 110 configured to convert the axial projection 108 (e.g., a two spatial dimension projection) into a rebinned axial projection 112 (e.g., a one spatial dimension projection), and a reconstructor 114 configured to generate an axial image 116 indicative of the object 104 from the rebinned axial projection 112. The axial image 116 may be displayed on a monitor 118 (that is part of a desktop or laptop computer) for human observation.

The object scanning apparatus 102 may be a third generation computed tomography (CT) scanner that comprises a stationary gantry 122, a rotating gantry 124, and a conveyor 126. The rotating gantry 124 is configured to rotate relative to the stationary gantry 122 about an axis of rotation 128 perpendicular to the plane of the page (e.g., into/out of the page). Similarly, the conveyor 126 is configured to convey the object 104 parallel to the axis of rotation 128 through a scanning field 130 (e.g., further into the page). In one example, a controller 120 is configured to regulate the motion of the conveyor 126. It will be understood to those skilled in the art that the controller 120 may receive input from a human observer and/or the controller 120 may function without human intervention.

It will be appreciated that the stationary gantry 122 need not be perfectly stationary and may, for example, be configured to translate along the axis of rotation 128. In the illustrated implementation, the rotating gantry 124 defines a generally cylindrical bore 132 having a diameter sized to receive an object to be scanned. The scanning field 130 is generally comprised within the cylindrical bore 132, and in an airport environment, for example, the bore 132 may have an inner diameter of roughly 2 feet, although other sizes and configurations are contemplated. It will be appreciated, however, that other types of scanners are also contemplated. For example, the techniques disclosed herein may be implemented in a fourth generation CT scanner.

The rotating gantry 124 comprises a radiation source 134 (e.g., an x-ray tube), and a detector array 136. In security applications, the radiation source 134 may generate a fan, cone, wedge, or other shaped beam of radiation that traverses the object 104 when the object 104 is in the scanning field 130. The rotating gantry 124, the radiation source 134, and the detector array 136 rotate about the object 104. In this way, projections from a variety of perspectives of a suitcase, for example, can be collected from a single scan of the object 104 to create a set of projections for the object 104. It will be appreciated that in another embodiment, the rotating gantry 124 is stationary and the object 104 is rotated.

Radiation that traverses the object 104 being scanned is detected by the detector array 136. Targets within the object 104 may cause various amounts of radiation to traverse the object 104 (e.g., creating areas of the high traversal and areas of low traversal within the object 104). For example, less radiation may traverse targets with a higher density and/or a higher atomic number (relative to densities and atomic numbers of other targets in the object). It will be appreciated that the changes in traversal may be used to create images of targets within the object 104. For example, if a suitcase, filled with clothes and a metal gun, passes through the object scanning apparatus 102, the gun may appear more prominently than the clothes (which may be virtually invisible), since the clothes are less dense than the gun (e.g., more radiation traverses the clothing than the gun).

In the example scanner 100, the data measurement system 106 is operably coupled to the object scanning apparatus 102, and is configured to collect information and data from the detector array 136. The data measurement system 106 may also be used to compile the collected data (from multiple views) into one or more axial projections 108 for the object 104. As an example, x-ray projections may be acquired at a plurality of angular positions (as the rotating gantry 124 rotates) with respect to the object 104.

The illustrated example scanner 100 also comprises the rebinner 110. The rebinner 110 is operably coupled to the data measurement system 106 and is configured to receive the axial projection(s) 108 and generate rebinned axial projection(s) 112. The rebinner 110 may use suitable analytical, iterative, and/or other rebinning techniques to convert the two spatial dimension axial projection(s) 108 to the one spatial dimension rebinned axial projection(s) 112, for example. In one example the axial projection(s) 108 may be rebinned using pin-mode rebinning. The rebinner 110 may also be configured to separate data based upon a focal spot 142 if the axial projection (108) comprises data related to a plurality of focal spots (e.g., a flying focal spot). For example, the radiation source 134 may be configured to adjust a focal spot 142 (e.g., a point on the radiation source 134 wherein radiation is emitted) and/or the radiation source may comprise multiple focal spots, and the rebinner 110 may separate axial projection 112 data based upon which of the plurality of focal spots emitted the detected x-rays. That is, the rebinned axial projection 112 may comprise data related to x-rays emitted from one focal spot 142 of the plurality of focal spots, for example.

In the example scanner 100, the reconstructor 114 is operably coupled to the rebinner 110, and is configured to receive the rebinned axial projection(s) 112 from the rebinner 110 and generate axial image(s) 116 indicative of the scanned object 104 using a suitable analytical, iterative, and/or reconstruction technique (e.g., backprojection from projection data space to image data).

Generally, rebinning and/or reconstruction techniques assume that the radiation passing from the radiation source 134 through the axis of rotation 128 (e.g., the center ray) intersects the detector array 136 at a specified location known as the center detector. That is, the rebinning and/or reconstruction techniques assume that, in most if not all measurements, the center ray will hit the detector array 136 at the same point and angle. The assumed, constant value of the center detector is used to calculate detector locations and radiation angles (e.g., fan angles) during rebinning and/or reconstruction. In order to mitigate the occurrence of artifacts (e.g., streaks at the edges of objects in the axial image(s) 116) that are caused by mismatch between the beamline geometry of the scanner and the geometry assumed by the rebinner 110 and/or reconstructor 114, the actual value of the center detector is periodically determined. If the actual value does not correspond (within a predetermined tolerance) to the assumed value, the object scanning apparatus 102, for example, may be adjusted to correspond to the assumed value.

It will be understood to those skilled in the art that for a scanner with a plurality focal spots, the techniques described herein may be applied to the respective focal spots. That is, a scanner may be comprised of a plurality of focus spots (because the radiation source 134 has multiple anodes in the radiation source 134 and/or because of alterations in an electromagnetic or other type of affecting field) and assumed values for the respective focal spots may be compared to their respective actual values (e.g., the assumed value for focal spot 1 is compared to the actual value for focal spot 1, the assumed value for focal spot 2 is compared to the actual value for focal spot 2, etc.).

In the example scanner 100, the actual value of the center detector is determined using a scanner calibrator 138. The scanner calibrator 138 may be configured to receive rebinned axial projection(s) 112 from the rebinner 110 when an object 104, comprising a target with known configurations (e.g., a phantom), is in the scanning field 130 of the object scanning apparatus 102. The rebinned axial projection(s) 112 may then be compared to an axial reprojection of a portion of the axial image(s) 116 of the target with known configurations to determine the actual value of the center detector, for example. If the actual value of the center detector is not within a predetermined tolerance of the assumed value, the scanner calibrator 138 may notify the object scanning apparatus 102, for example, to adjust the radiation source 134 and/or the detector array 136.

In the illustrated example scanner 100, the object 104 may be positioned on the conveyor 126 through existing diagnostic software in the scanner, and a target position verifying component 140 may be configured to verify the position of the object 104 in the scanning field 130. In one example, the target position verifying component 140 is configured to measure the length and orientation of the object 104 in the scanning field 130 (when less than all of the object 104 is conveyed into the scanning field) and compare it with a predetermined value for the length and orientation of the object 104 that should be in the scanning field 130 when the actual value of the center detector is being determined. If, after a comparison, the target position verifying component 140 determines that the object 104 is not in a predetermined position (e.g., the position at which a predetermined value related to the length of the object (104, 200) inside the scanning field (130) is approximately equal to the measured length and/or the position at which a second predetermined value related to the orientation of the object (104, 200) inside the scanning field (130) is approximately equal to the measured orientation), the target position verifying component 140 may notify the controller 120 to reposition the object 104 and/or send an error message to a human observer through the monitor 118, for example.

Determining the center detector using the techniques herein disclosed may promote efficiency and costs. For example, using techniques disclosed in prior art, an object scanning apparatus (e.g., 102 in FIG. 1) had to be powered down while a service engineering, or other user, crawled into the scanning field (e.g., 130 in FIG. 1) to place an object (e.g., 104 in FIG. 1) in a specified location. Using the techniques herein disclosed, time may be saved and there may be less disruption of scanner operations because a service technician does not have to enter the scanning field, and the scanning apparatus does not have to be powered down (to reduce radiation exposure). Additionally, the techniques herein disclosed may reduce production costs of the scanner 100. Instead of a unique object (e.g., target) specifically designed for determining the center detector (as disclosed in prior art), the object (e.g., an image quality phantom) may be designed for and/or already used in other testing/calibration procedures, such as image quality testing. Therefore, the cost of producing the scanner 100 may be reduced since fewer phantoms may need to be manufactured.

Figure 2:
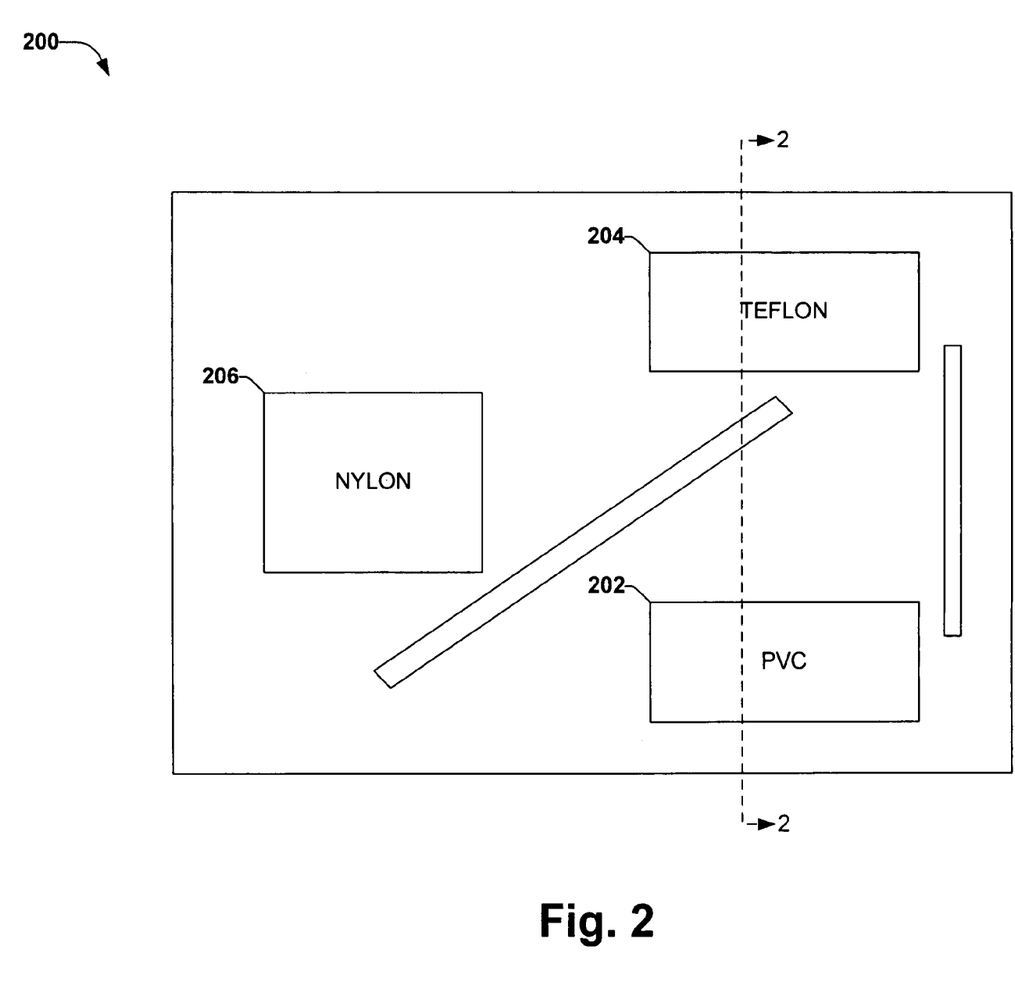
FIG. 2 depicts an example phantom that may be used to determine the center detector of a detector array.

FIG. 2 illustrates an example object 200 (e.g., 104 in FIG. 1) that may be used to determine a center detector on an object scanning apparatus (e.g., 102 in FIG. 1). In one example, the object 200 is an image quality phantom (IQP). The object 200 may comprise targets of known configuration. In the illustrated object 200, the targets that are used to determine the center detector are a cylinder of polyvinyl chloride (PVC) 202 and a cylinder of Teflon 204. The object 200 may also comprise other targets, such as a nylon box 206, that may not be used to determine the center detector but may be used for other testing, such as image quality testing, for example.

In one embodiment, the two targets used to determine the center detector are in parallel so that two measurements can be acquired from one data set (e.g., axial scans about a single cross-sectional area of the object). That is, the measurements from the two targets can be compared to verify the accuracy of the measured, actual value (e.g., providing a consistency check).

It will be appreciated that other configurations of the object 200 are also contemplated. For example, the object 200 may comprise one target (instead of two) that is used to determine the center detector. Additionally, the one or more targets may be comprised of different material (than PVC, Teflon, or nylon) and/or configured into shapes other than cylinders or boxes.

Figure 3:
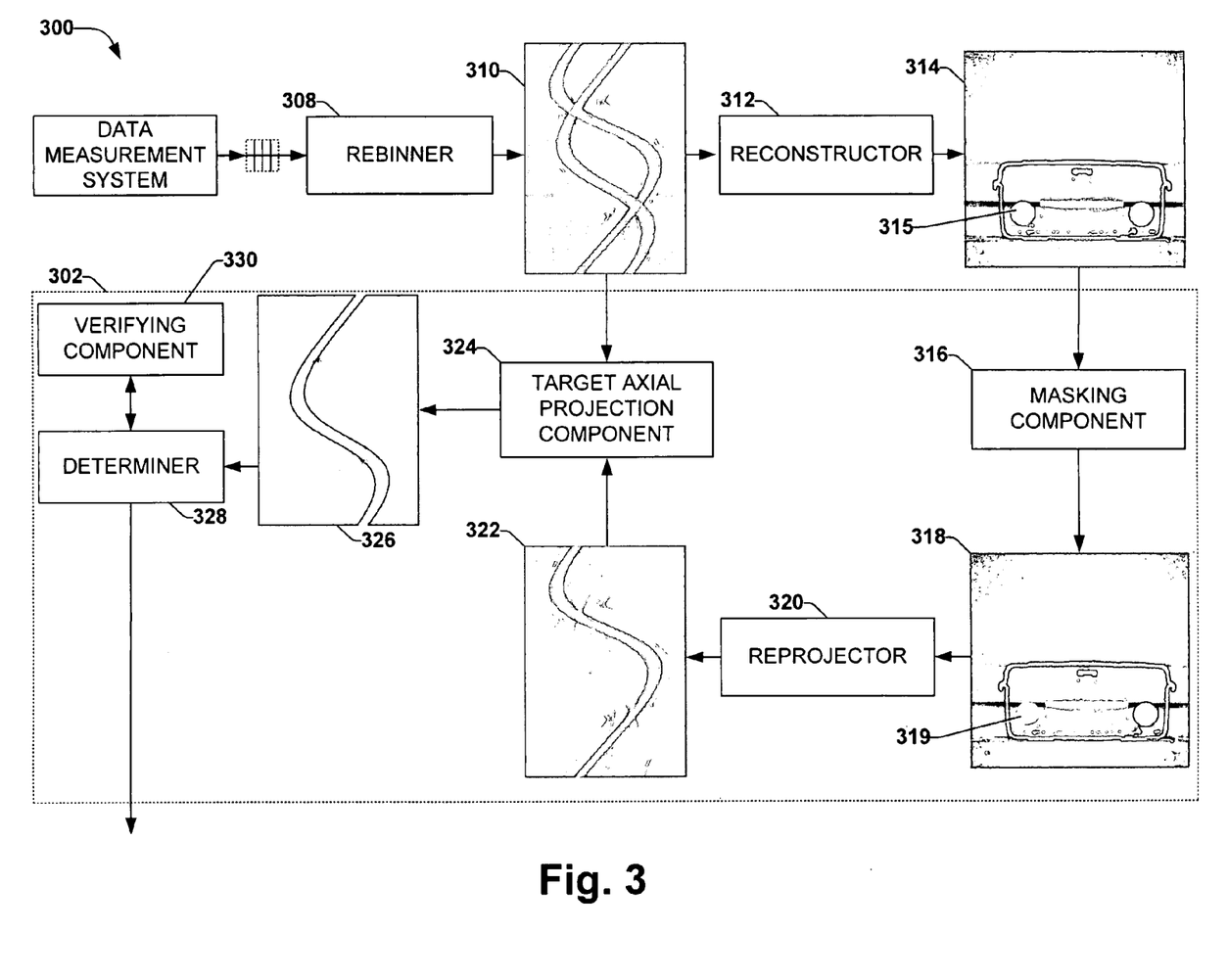
FIG. 3 is a schematic block diagram illustrating one or more components of a scanner calibrator configured to determine the center detector of a detector array.

FIG. 3 is a schematic block diagram 300 illustrating, among other things, one or more components of an example scanner calibrator 302 (e.g., 138 in FIG. 1) that may be configured to determine a center detector and calibrate a scanner (e.g., 100 in FIG. 1) based upon the determination. FIG. 3 also illustrates graphical representations of data that may be produced by the one or more components that comprise the scanner calibrator 302.

The example scanner calibrator 302 comprises a masking component 316 that is operably coupled to a reconstructor 312 (e.g., 114 in FIG. 1), and is configured to receive an axial image 314 (e.g., 116 in FIG. 1) of a cross sectional area of an object comprises one or more targets 315 with known configurations (e.g., object 200 taken along line 2-2 in FIG. 2). The masking component 316 may also be configured to mask one or more (predetermined) targets 315 in the axial image 314 of the object with known configurations and produce a masked axial image 318. In one example, the masking component 316 thresholds the axial image 314 and analyzes the axial image 314 to locate a predetermined target 315. For example, the masking component 316 may know the approximate location of the predetermined target 315 in the object since the object has known configurations, and the masking component 316 may pinpoint the target 315 based upon characteristics of the object that distinguish it from surrounding objects (e.g., the brightness of the target 315 on the axial image 314, the shape of the target 315, etc.).

In one embodiment, the masking component 316 masks the predetermined target 315 by setting the pixels that comprise the predetermined target 315 to a value corresponding to an image offset (e.g., making that predetermined target 315 disappear or otherwise be hidden from the axial image 314). In the illustrated example 300, a white circle on the left side of the axial image 314 is masked by the masking component 316 so that a darker circle 319 (relative to the white circle) appears in the masked axial image 318.

The scanner calibrator 302 also comprises a reprojector 320 that is operably coupled to the masking component 316 and is configured to receive the masked axial image 318 and generate an axial reprojection 322 of the masked axial image 318. It will be understood to those skilled in the art that the reprojector 320 converts data that comprises the masked axial image 318 into an axial reprojection 322. Since the predetermined target 315 is masked in the masked axial image 318, data related to the predetermined target 315 may not be presented in the axial reprojection. In one example, the data from the masked axial image 318 is represented as sinograms in the axial reprojection 322.

The example scanner calibrator 302 also comprises a target axial projection component 324. The target axial projection component 324 is in operable communication with the reprojector 320 and is configured to receive the axial reprojection 322. The target axial projection component 324 is also in operable communication with a rebinner 308 (e.g., 110 in FIG. 1) and is also configured to receive a rebinned axial projection 310 corresponding to the axial image 314 that is produced by the reconstructor 312. That is, the target axial projection component 324 receives the rebinned axial projection 310 that is used by the reconstructor 312 to create the axial image 314. In one example, the target axial projection component 324 receives the rebinned axial projection 310 before it receives the axial reprojection 322 (since the axial reprojection 322 is a partial derivation of the rebinned axial projection 310), and the target axial projection component 324 is configured to store the rebinned axial projection 310 until the axial reprojection 322 is received. It will be appreciated that the rebinner 308 may also store the rebinned axial projection 310 until the axial reprojection 322 is received by the target axial projection component 324.

The target axial projection component 324 may also be configured to compare the axial reprojection 322 to the rebinned axial projection 310 to produce a target axial projection 326. In one example, the target axial projection 326 is the difference between the data comprising the rebinned axial projection 310 and data comprising the axial reprojection 322. It will be understood to those skilled in the art that the target axial projection 326 should represent data related to the predetermined target that was masked by the masking component 316.

The scanner calibrator 302 also comprises a determiner 328 that is configured to receive the target axial projection 326 and determine the actual value of the center detector as a function of the projection 326. In one embodiment, a commonly used technique, known to those skilled in the art as pin calibration, is used to compute the center detector. For example, algorithms may be used to compute the values of the center detector for n number of views of the target 315 based upon the target axial projection 326. The values of the center detector may be fit using a non-linear fitting technique, for example, by finding an equation that describes the value of the center detector for any particular view. Once an equation for the value of the center detector is determined, the residual error between the fit and the actual values of the center detector for the n number of views may be computed. In one embodiment, the determiner 328 may remove up to a predetermined number of views (from the target axial projection 326) that comprise a residual error that is greater than a predetermined threshold (e.g., outlying views) and refit the values of the center detector for views that have not been excluded. It will be understood to those skilled in the art that removing outlying views may reduce spikes that are caused by negative projections, for example, and improve the accuracy of the fit. The actual value of the center detector (e.g., the centroid) is obtained as a fit parameter.

It will be appreciated that the scanner calibrator 302 may also determine the actual value of the center detector based upon a second predetermined target in the object, and a verifying component 330 may verify that the actual value based upon a first predetermined target and the actual value based upon the second predetermined target are similar (e.g., within a margin of error), for example. In one embodiment, the verifying component 330 also averages the actual value as determined based upon the first predetermined target with the actual value as determined based upon the second predetermined target and transmits the averaged value of the center detector back to the determiner 328. It will be appreciated that the verifying component may also be configured to send an error message to an object scanning apparatus (e.g., 102 in FIG. 1), for example, if the actual values are outside of a margin of error.

Once the determiner 328 has determined the actual center detector and/or an average value of the center detector is received by the verifying component 330, the determiner 328 may compare the actual/averaged value to an assumed value (e.g., used by the rebinner 308 and/or reconstructor 312). If the actual/averaged value is not within a predetermined threshold of the assumed value, the determiner 328 and notify the object scanning apparatus to adjust a radiation source (134 in FIG. 1) and/or a detector array (136 in FIG. 1), for example. It will be appreciated that the determiner 328 may also notify other components of a scanner (e.g., 100 in FIG. 1) and/or make adjustments to other components of the scanner. For example, the determiner 328 may adjust the assumed value of the center detector to correspond to the actual/averaged value of the center detector.

Figure 4:
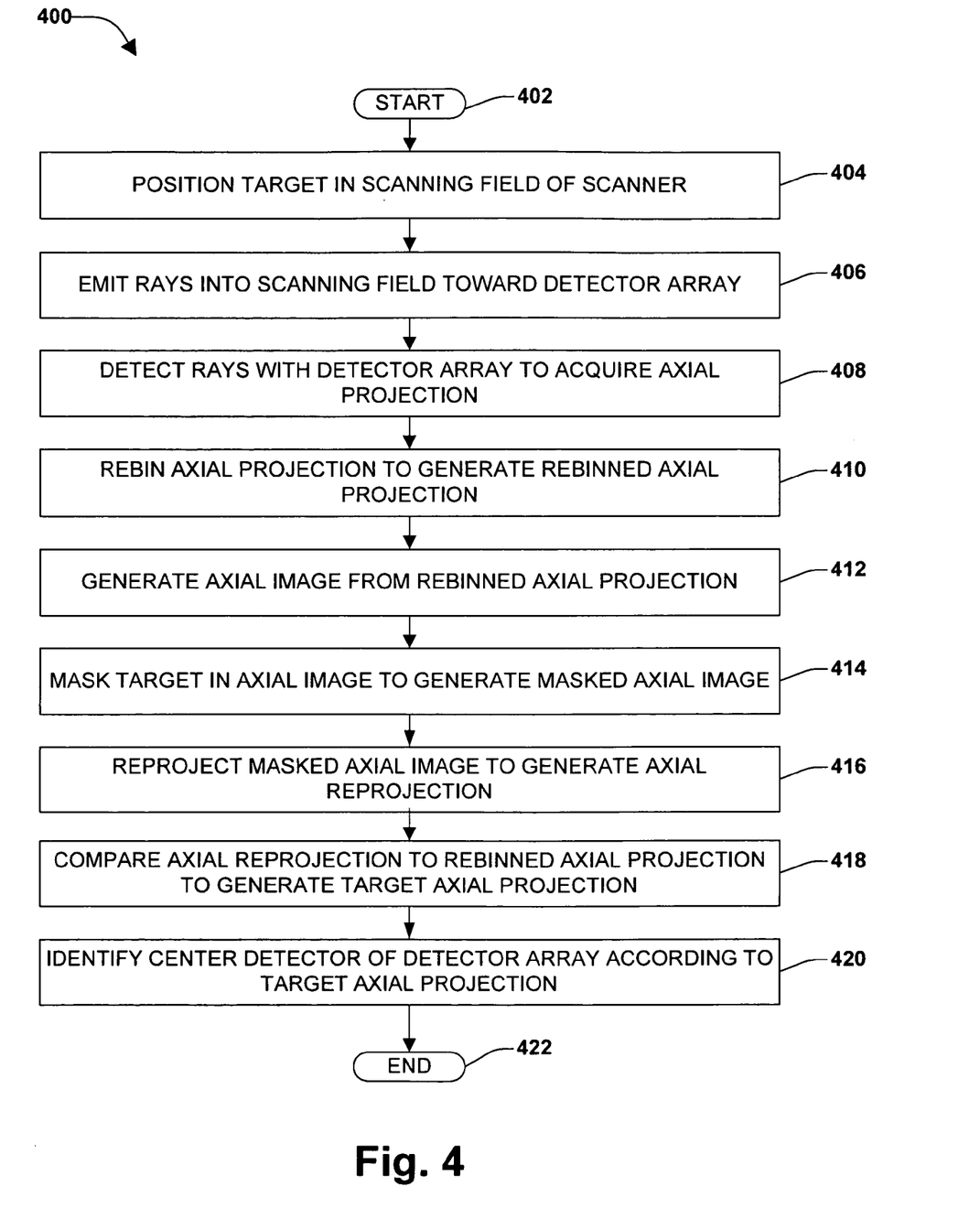
FIG. 4 is a flow diagram illustrating an example method for detecting a center detector in a detector array of a scanner using a target.

FIG. 4 illustrates an exemplary method 400 of detecting a center detector in a detector array of a scanner using a target. The method begins at 402, and the target is positioned in a scanning field of the scanner at 404. In one embodiment, the target is placed on a conveyor and conveyed into the scanning field of the scanner. A positioning procedure may be used to verify the position of the target in the scanning field. For example, the conveyor may be configured to convey less than the entire target into the scanning field, and the scanner may be configured to compare a measurement the length of the target in the scanning field to a predetermined value and/or compare a measurement of the orientation of the object with a second predetermined value.

At 406, rays are emitted into the scanning field toward the detector array, and at 408, the rays are detected by the detector array to acquire an axial projection representing an axial view of the scanning field. In one example, a portion of the scanner (e.g., a ray source and the detector array) rotates about the scanning field and the axial projection comprises data related to multiple views of the scanning field along a single axis. It will be appreciated that less than all of the emitted rays may be detected by the detector array because the target may absorb some of the radiation.

At 410, the axial projection is rebinned to generate a rebinned axial projection using techniques known to those skilled in the art. In one embodiment, rebinning causes two spatial dimension data (e.g., cone beam data) to be converted to one spatial dimension data (e.g., fan beam data) that can be represented as a sinogram in the rebinned axial projection. It will be appreciated that the rebinning techniques use a value of a specified location, commonly referred to as center detector, to calculate detector locations and fan angles. This value (e.g., an assumed value) is intended to correspond to a center ray that passes from a radiation source to the detector array through an axis of rotation. If the actual beamline geometry and the assumed beamline geometry (based upon the assumed value of the center detector) do not correspond, artifacts may be produced in the rebinned axial projection.

At 412, an axial image is generated from the rebinned axial projection using a suitable analytical, iterative, and/or other reconstruction technique (e.g., backprojecting from projection space to image space). The reconstruction techniques may also use the assumed value of the center detector to convert the rebinned axial projection into the axial image.

At 414, the target in the axial image of the scanning field is masked to generate a masked axial image. In one embodiment, the image is thresholded, analyzed to locate the target, and the pixels that represent the target are set to a value of the image offset to mask the target. A target may be located in the axial image based upon known configurations of the target. For example, the approximate location of the target may be known (based upon its placement on the conveyor) and the exact location of the target may be determined based upon contrast in the image (e.g., a light colored target surround by a darker region in the scanning field). In another example, the target is made of a material with known absorption patterns, and the location of the target is determined based upon the amount of x-rays absorbed in the region of the axial image that comprises the target.

At 416, the masked axial image is reprojected to generate an axial reprojection using reprojection techniques known to those skilled in the art. It will be appreciated that the axial reprojection generally comprises the data in the rebinned axial projection except data that is related to the target.

At 418, the axial reprojection is compared to the rebinned axial projection (from 410) to generate a target axial projection of the target. That is, data related to the target comprised in the rebinned axial projection may be isolated from data related to other objects in the scanning field, for example. In one embodiment, the data in the rebinned axial projection is subtracted from the data in the axial reprojection to isolate projection data related to the target.

At 420, the center detector of the detector array is identified according to the target axial projection through techniques known to those skilled in the art (e.g., pin calibration techniques). In one example, center detectors are computed for n number views (depicted in the target axial projection), and the computed center detector is fit to an aggregated center detector. Residual errors between the fit and computed center detectors for the n number of views may also be computed to promote accuracy and reduce bad data, for example. If one or more of the views have a residual error greater than some threshold, the view(s) with the greater residual error may be excluded, and the computed center detectors of the remaining views may be refit to recompute the aggregated computed center detector (e.g., the actual value of the center detector). The method ends at 422.

It will be appreciated that the scanner may scan more than one target at once and the acts of masking 414, reprojecting 416, comparing 418, and identifying 420 may be repeated to determine the center detector for each of the scanned targets. In one embodiment, the aggregated computed center detectors for the targets may be averaged to determine the actual value of the center detector.

It will be understood to those skilled in the art that the actual value of the center detector may be compared to the assumed value of the center detector (that is used by the rebinner and reconstructor). If the actual value is not within some tolerance of the assumed value, the radiation source, detection array, assumed value, etc., may be adjusted so that the actual value corresponds to the assumed value.

It will also be understood to those skilled in the art that the techniques disclosed herein may be repeated for a ray source with a plurality of focal spots. That is, the axial projection may be separated based upon which of the plurality of focal spots emitted the detected x-rays, and the rebinned axial projection may comprise data related to less than all of the focal spots. The assumed center detector values may then be compared to the actual center detector values for the respective focal spots. In this way, each of the focal spots may be calibrated, for example.

Figure 5:
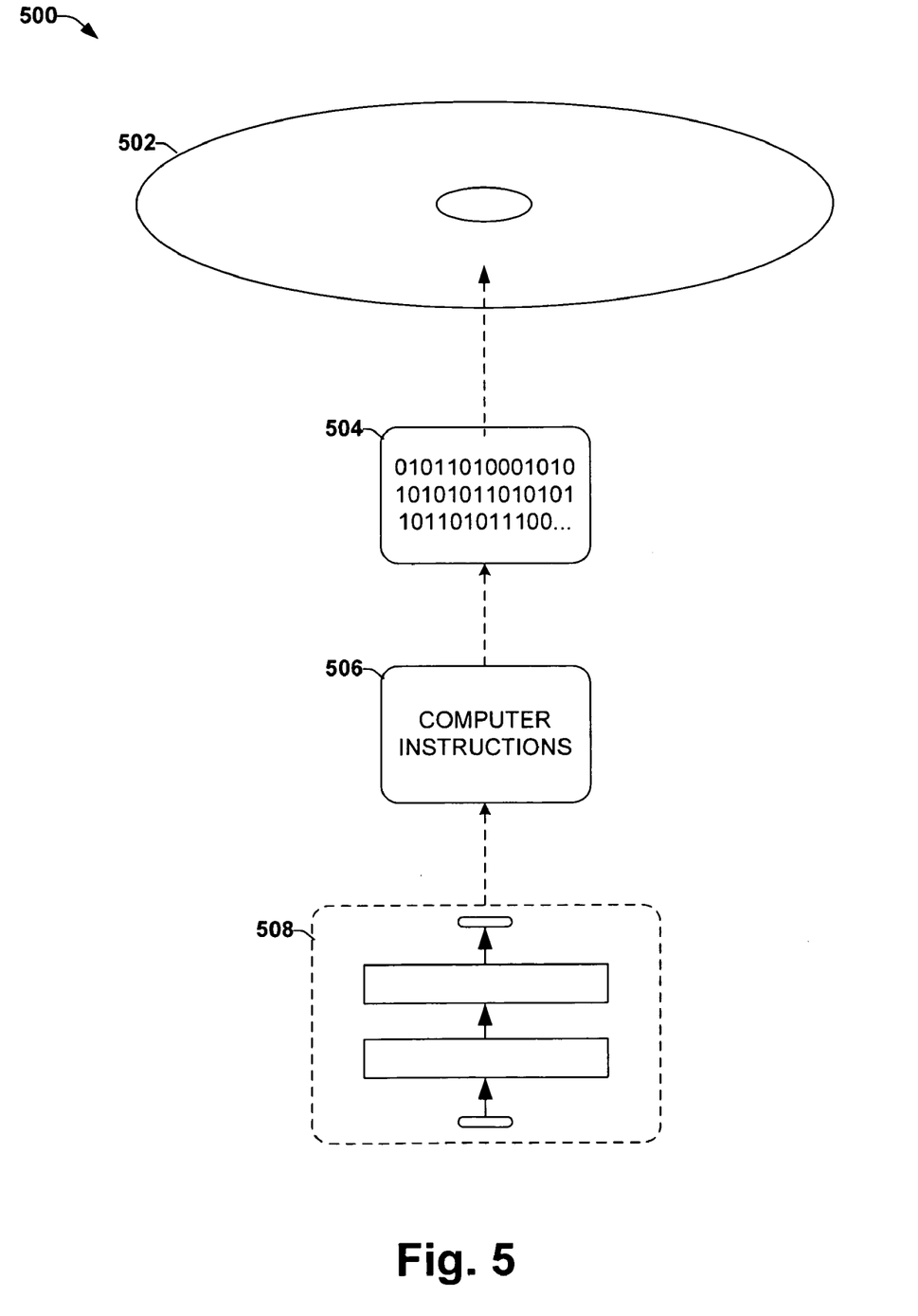
FIG. 5 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An exemplary computer-readable medium that may be devised in these ways is illustrated in FIG. 5, wherein the implementation 500 comprises a computer-readable medium 502 (e.g., a CD-R, DVD-R, or a platter of a hard disk drive), on which is encoded computer-readable data 504. This computer-readable data 504 in turn comprises a set of computer instructions 506 configured to operate according to one or more of the principles set forth herein. In one such embodiment 500, the processor-executable instructions 506 may be configured to perform a method, such as the exemplary method 400 of FIG. 4, for example. In another such embodiment, the processor-executable instructions 506 may be configured to implement a system, such as at least some of the exemplary scanner 100 of FIG. 1, for example. Many such computer-readable media may be devised by those of ordinary skill in the art that are configured to operate in accordance with the techniques presented herein.

The application has been described with reference to various embodiments. Modifications and alterations will occur to others upon reading the application. It is intended that the claimed subject matter be construed as including all such modifications and alterations, including insofar as they come within the scope of the appended claims and the equivalents thereof.

What is claimed is:

1. A scanner comprising:
 a radiation source configured to emit radiation into a scanning field of the scanner;
 a detector array configured to detect radiation emitted into the scanning field that has traversed an object situated therein; and
 a scanner calibrator configured to determine a position of a center detector of the detector array based upon a comparison of an axial projection of the object to an axial reprojection of a masked axial image of the object.

2. The scanner of claim 1, the scanner calibrator configured to:
 generate a rebinned axial projection from the axial projection;
 generate a target axial projection based upon a comparison of the rebinned axial projection to the axial reprojection;
 determine the position of the center detector of the detector array using the target axial projection; and
 calibrate the scanner according to the determined position of the center detector of the detector array.

3. The scanner of claim 2, comprising:
 a target position verifying component configured to verify a position of the object in the scanning field.

4. The scanner of claim 3,
 the target position verifying component configured to verify the position of the object based upon at least one of a comparison of a length of the object inside the scanning field to a first predetermined value and a comparison of an orientation of the object inside the scanning field to a second predetermined value.

5. The scanner of claim 1, the scanner calibrator comprising:
   a masking component configured to mask a target within an axial image of the object yielded from the axial projection to generate the masked axial image;
   a reprojector configured to reproject the masked axial image to generate the axial reprojection;
   a target axial projection component configured to compare the axial reprojection to at least one of the axial projection and a rebinned axial projection yielded from the axial projection to generate a target axial projection; and
   a determiner configured to determine the position of the center detector of the detector array using the target axial projection.

6. The scanner of claim 5, the determiner configured to:
   compute a centroid of the target for respective axial views;
   fit the centroid computed for respective axial views to an aggregated computed centroid; and
   if at least one computed centroid of at least one axial view differs from the aggregated computed centroid by an error threshold:
      exclude the at least one axial view;
      recompute the centroid of the target for respective non-excluded axial views; and
      refit the centroid computed for respective non-excluded axial views to recompute the aggregated computed centroid.

7. The scanner of claim 1,
   the object comprising at least a first target and a second target and
   the scanner calibrator comprising a verifying component configured to compare a first target axial projection of the first target and a second target axial projection of the second target to verify the determined position of the center detector.

8. A target detector system configured to generate a target axial projection from an axial projection representing a target detected in a scanning field by a detector array of in a scanner, comprising:
   a reconstructor configured to generate an axial image from at least one of the axial projection and a rebinned axial projection yielded from the axial projection;
   a masking component configured to mask the target in the axial image to generate a masked axial image;
   a reprojector configured to reproject the masked axial image to generate an axial reprojection; and
   a target axial projection component configured to compare the axial reprojection to at least one of the axial projection and the rebinned axial projection to generate the target axial projection.

9. The system of claim 8, comprising a rebinner configured to rebin the axial projection to generate the rebinned axial projection, the rebinning comprising a cone beam to fan beam rebinning.

10. The system of claim 8, comprising: a determiner configured to identify a position of a center detector of the detector array using the target axial projection.

11. The system of claim 10,
   an object under examination by the scanner comprising at least two targets and
   the scanner comprising a verifying component configured to compare a first target axial projection of the first target and a second target axial projection of the second target to verify the position of the center detector.

12. The system of claim 8, the axial projection comprising data representing a plurality of views of the target, respective views indicative of a different rotational position of the detector array relative to an object under examination by the scanner.

13. A method of detecting a position of a center detector in a detector array of a scanner using a target, the method comprising:
   emitting x-rays toward the target positioned in a scanning field of the scanner;
   detecting the x-rays with the detector array to acquire an axial projection at least partially indicative of the target;
   generating an axial image from at least one of the axial projection and a rebinned axial projection yielded from the axial projection;
   masking the target in the axial image to generate a masked axial image;
   reprojecting the masked axial image to generate an axial reprojection;
   comparing the axial reprojection to the rebinned axial projection to generate a target axial projection; and
   identifying the position of the center detector of the detector array using the target axial projection.

14. The method of claim 13, comprising:
   verifying a position of the target in the scanning field.

15. The method of claim 14, verifying the position of the target comprising:
   measuring a length of the target inside the scanning field;
   comparing the measured length to a predetermined length that is supposed to be in the scanning field when the axial projection is acquired; and
   adjusting the position of the target if the measured length is not within a predetermined tolerance of the predetermined length.

16. The method of claim 14, verifying the position of the target comprising:
   measuring an orientation of the target inside the scanning field;
   comparing the measured orientation to a predetermined orientation that is supposed to be in the scanning field when the axial projection is acquired; and
   adjusting the position of the target if the measured orientation is not within a predetermined tolerance of the predetermined orientation.

17. The method of claim 13, comprising rebinning the axial projection to generate the rebinned axial projection, the rebinning comprising a cone beam to fan beam rebinning.

18. The method of claim 13, identifying the position of the center detector comprising:
   generating data representing a plurality of views of the target, a first view representative of the target from a first angle and a second view representative of the target from a second, different angle;
   computing a centroid of the target for respective views;
   fitting the centroid computed for respective views to an aggregated computed centroid; and
   if at least one computed centroid of at least one view differs from the aggregated computed centroid by an error threshold:
      excluding the at least one view;
      recomputing the centroid of the target for respective non-excluded views; and
      refitting the centroid computed for respective non-excluded views to recompute the aggregated computed centroid.

19. The method of claim 13, comprising positioning the target in the scanning field of the scanner while x-rays are being emitted into the scanning field.

20. The method of claim 13, comprising:
separating data yielded from x-rays emitted from a first focal spot of the scanner from data yielded from x-rays emitted from a second focal spot of the scanner, data yielded from x-rays emitted from the first focal spot yielding a first axial projection and data yielded from x-rays emitted from the second focal spot yielding a second axial projection; and
performing the acts of generating, masking, reprojecting, comparing, and identifying for both the first and second axial projections.

\* \* \* \* \*

UNITED STATES PATENT AND TRADEMARK OFFICE
CERTIFICATE OF CORRECTION

PATENT NO. : 8,411,814 B2  
APPLICATION NO. : 13/126608  
DATED : April 2, 2013  
INVENTOR(S) : Ram C. Naidu, Sergey B. Simanovksy and David Schafer Page 1 of 1

It is certified that error appears in the above-identified patent and that said Letters Patent is hereby corrected as shown below:

In the Claims:

Claim 8, Column 11, Line 39: Delete the word "in" after "field by a detector array of"

Signed and Sealed this  
Twenty-eighth Day of May, 2013

Teresa Stanek Rea  
*Acting Director of the United States Patent and Trademark Office*